US008553208B2

(12) United States Patent
Linares et al.

(10) Patent No.: US 8,553,208 B2
(45) Date of Patent: *Oct. 8, 2013

(54) RETAIL COMPATIBLE DETECTION OF CVD GROWN DIAMOND

(75) Inventors: Robert C. Linares, Sherborn, MA (US); Patrick J. Doering, Holliston, MA (US)

(73) Assignee: SCIO Diamond Technology Corporation, Greer, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/491,301

(22) Filed: Jun. 7, 2012

(65) Prior Publication Data

US 2012/0242977 A1   Sep. 27, 2012

Related U.S. Application Data

(63) Continuation of application No. 12/463,106, filed on May 8, 2009, now Pat. No. 8,213,000.

(60) Provisional application No. 61/051,929, filed on May 9, 2008.

(51) Int. Cl.
*G01N 21/00* (2006.01)

(52) U.S. Cl.
USPC .......................................................... 356/30

(58) Field of Classification Search
USPC .......................................................... 356/30
See application file for complete search history.

(56) References Cited

U.S. PATENT DOCUMENTS

| | | | |
|---|---|---|---|
| 4,573,761 A | 3/1986 | McLachlan et al. | |
| 5,801,819 A | 9/1998 | Spear et al. | |
| 5,811,817 A | 9/1998 | Ravich | |
| 5,880,504 A | 3/1999 | Smith et al. | |
| 6,144,448 A * | 11/2000 | Mitoma | 356/317 |
| 7,105,822 B1 | 9/2006 | Beesley | |
| 7,800,740 B2 | 9/2010 | Gumpesberger | |
| 8,134,694 B2 | 3/2012 | Linares et al. | |
| 8,213,000 B2 | 7/2012 | Linares et al. | |
| 2010/0026985 A1 | 2/2010 | Linares et al. | |
| 2010/0053597 A1 | 3/2010 | Linares et al. | |
| 2012/0170019 A1 | 7/2012 | Linares et al. | |

FOREIGN PATENT DOCUMENTS

| | | |
|---|---|---|
| GB | 2 244 329 A * | 4/1990 |
| WO | WO 02/06797 * | 1/2002 |

OTHER PUBLICATIONS

"U.S. Appl. No. 12/463,106, Non Final Office Action mailed Mar. 11, 2011", 7 pgs.
"U.S. Appl. No. 12/463,106, Notice of Allowance mailed Feb. 23, 2012", 7 pgs.
"U.S. Appl. No. 12/463,106, Response filed Sep. 28, 2011 to Non Final Office Action mailed Mar. 11, 2011", 7 pgs.
"U.S. Appl. No. 12/463,106, Response to Rule 312 Communication mailed Jun. 1, 2012", 2 pgs.
"U.S. Appl. No. 12/463,152, Non Final Office Action mailed Feb. 25, 2011", 5 pgs.

(Continued)

*Primary Examiner* — Kara E Geisel
(74) *Attorney, Agent, or Firm* — Schwegman Lundberg & Woessner, P.A.

(57) ABSTRACT

A system includes a radiation source to provide short wavelength light. A holder positions a table of a gemstone to receive the light. A detector is positioned to receive fluorescent light from the gemstone when the gemstone is a CVD grown gemstone.

20 Claims, 3 Drawing Sheets

(56) References Cited

OTHER PUBLICATIONS

"U.S. Appl. No. 12/463,152, Notice of Allowance mailed Nov. 7, 2011", 7 pgs.

"U.S. Appl. No. 12/463,152, Response filed Aug. 18, 2011 to Non Final Office Action mailed Feb. 25, 2011", 6 pgs.

"U.S. Appl. No. 13/418,122, Non Final Office Action mailed Jan. 8, 2013", 7 pgs.

"U.S. Appl. No. 13/418,122, Notice of Allowance mailed Apr. 18, 2013", 8 pgs.

"U.S. Appl. No. 13/418,122, Response filed Apr. 8, 2013 to Non Final Office Action mailed Jan. 8, 2013", 6 pgs.

Wang, Wuyi, et al., "Latest-Generation CVD-Grown Synthetic Diamonds from Apollo Diamond Inc.", Gems & Gemology, Winter 2007, vol. 43, No. 4, (2007), pp. 294-312.

\* cited by examiner

RETAIL COMPATIBLE DETECTION OF CVD GROWN DIAMOND

CROSS-REFERENCE TO RELATED APPLICATIONS

This application is a continuation of U.S. application Ser. No. 12/463,106, filed May 8, 2009 which claims priority to U.S. Provisional Application Ser. No. 61/051,929, filed May 9, 2008, the entire disclosures of which are incorporated by reference herein.

BACKGROUND

Chemical vapor deposition grown diamonds can be difficult to distinguish from mined diamonds using conventional techniques. Detection of CVD diamond is of importance to the diamond industry to prevent the fraudulent sale of CVD diamond as natural diamond, and to enable the detection of CVD diamond for the purpose of ensuring that there is no misrepresenting natural as CVD diamond. Further, the detection of CVD diamond may be useful for protecting intellectual property rights.

The detection of CVD diamond is difficult and laborious due to the fact that multiple instruments are needed. Such instruments are used to first determine that the diamond in question is a type II A. Colorless cvd diamonds currently are type II A which indicates a very low nitrogen level. The instruments are then used for testing for the presence of N-V centers, which are a substitutional nitrogen atom adjacent to a carbon vacancy. Finally, instruments are used to microscopically view diamonds for features such as strain. All of these tests are required to raise the certainty that a diamond is natural or cvd. None of these tests are complete in themselves, as the presence of N-V centers is rare in natural diamonds, but does occur. Such N-V centers fluoresce at red-orange wavelengths due to it's two main emission peaks centered at 575 and 637 nm. The purer the diamond the weaker the fluorescence. The fluorescence can also be seen by illuminating the diamond with short wavelength ultraviolet light in an expensive instrument such as the "Diamond View". The detection process is long and difficult for large pure stones and nearly impossible for small stones.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
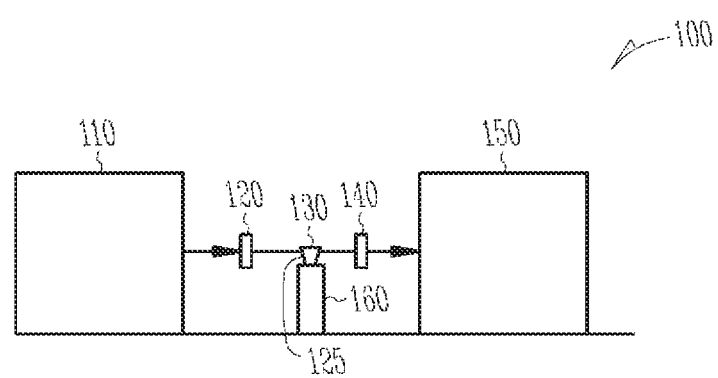
FIG. 1 is a block diagram of a system for detecting CVD grown diamonds in a retail setting according to an example embodiment.

A system 100 in FIG. 1 may be used to detect CVD grown diamond. System 100 may be formed in a size that is compatible for deployment in a jewelry retail store and be operated by relatively unskilled personnel. System 100 may utilize the presence of an N-V center in a CVD grown diamond. At 110, a radiation source provides short wavelength light. The short wavelength light may be provided by a green or blue laser, such as a commercially available semiconductor laser which emits at 405 or 532 nm. Many other wavelengths may be used that cause fluorescence of diamonds with N-V centers, such as wavelengths in the 400 to 550 nm range, and may include portions of the UV range of 10 to 400 nm, or at least the upper portions of the UV range. Other sources that provide suitable wavelength light may also be used.

A fiber optic delivery system or lens 120 may be used to provide short wavelength radiation to a holder 125 to position a table of a gemstone 130 at a predetermined distance from the light. The holder 125 may be adapted with suitable fixtures such as clamps or platforms with indentations to hold a loose gemstone or gemstones, as well as a piece of jewelry containing one or more gemstones such as diamonds. The laser in one embodiment is highly focused on the crystal surface of the gemstone. A fitter(s) (or spectrometer) 140 may be used to separate the laser light from the PL light (photoluminescence).

The presence of N-V centers would result in emission bands centered at about 575 and/or 637 nm, and the filters can be used to allow detection of these wavelengths. A detector 150 may be positioned to receive and detect the PL light, in one embodiment, a thermoelectric cooler 160 may be used to cool the gemstone. The cooler 160 may be integrated with the holder 120 in one embodiment. Alternatively to a thermoelectric cooler, a cooling media such as liquid nitrogen or dry ice may be positioned proximate to the gemstone to cool the gemstone.

Detector 150 may contain suitable electronics and metering to indicate the nature and type of the diamond from the detected PL light. Detector 150 may be used in conjunction with microscopic examination to confirm the natural or CVD origins of the gemstone. Further filtering of wavelengths may also be used to detect treated natural stones or high pressure high temperature created stones. In a further embodiment, handling of the stones may be automated so that they could be continuously measured and recorded without human handling.

In further embodiments, filters or an inexpensive spectrometer may be used to separate wavelengths to ensure that the laser light and the PL light are separated. A suitable covering may be used to eliminate stray room light from entering the detector and laser light from straying to the outside. Safety interlocks may be provided to shut down the laser in the event the cover is removed. Holder 125 may be made large enough to hold several sizes of stones. Control circuitry and sensors may be included to indicate a pass, fail, or further inspection notice for the tester.

Figure 2:
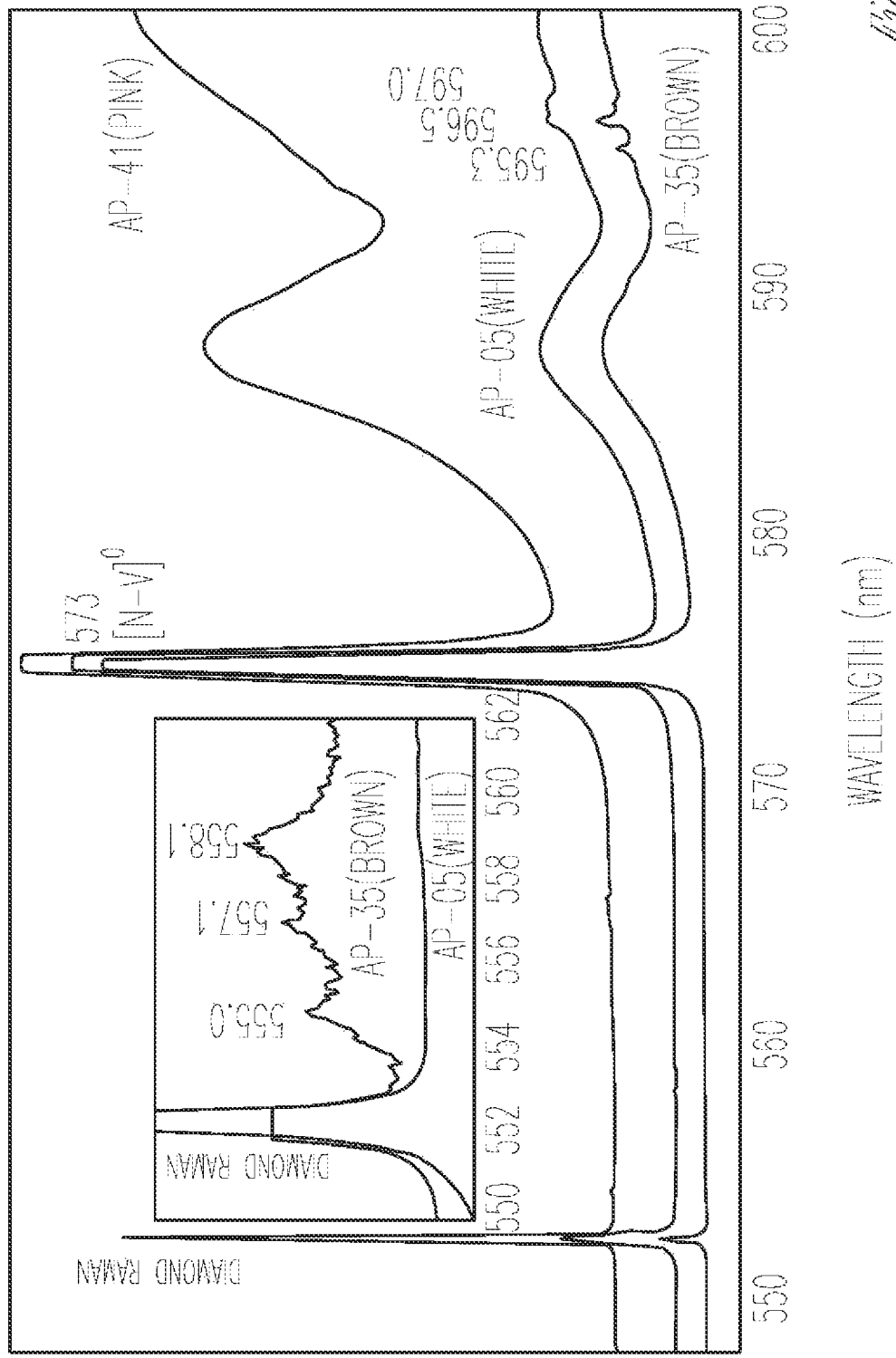
FIG. 2 is a graph illustrating photo luminescence (PL) of white, brown and pink cvd diamonds.

FIG. 2 is a graph illustrating photo luminescence (PL) of white, brown and pink cvd diamonds.

Some embodiments may be made fairly inexpensive and have a fairly small footprint, and may be easy to operate, making them suitable for use and operation by a store clerk in a retail store.

Figure 3:
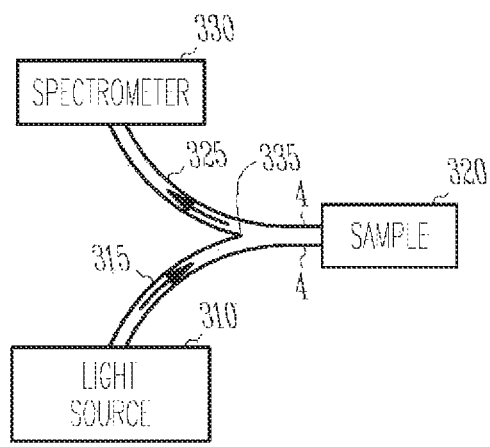
FIG. 3 is a block diagram of an alternative system for detecting CVD grown diamonds in a retail setting according to an example embodiment.

FIG. 3 is an alternative system 300 may be used to detect CVD grown diamond. System 300 may be formed in a size that is compatible for deployment in a jewelry retail store and be operated by relatively unskilled personnel. System 300 may utilize the presence of an N-V center in a CVD grown diamond. At 310, a light source provides short wavelength light to an optical fiber 315 that may be optimized to transmit the short wavelength light. The short wavelength light may be provided by a green or blue laser, such as a commercially available semiconductor laser which emits at 405 or 532 nm. Many other wavelengths may be used that cause fluorescence of diamonds with N-V centers, such as wavelengths in the 400 to 550 nm range, and may include portions of the UV range of 10 to 400 nm, or at least the upper portions of the UV range. Other sources that provide suitable wavelength light may also be used.

The optical fiber 315 provides the light from light source 310 to a sample holder 320 to position a table of a gemstone at a predetermined distance from the light The sample holder 320 may be adapted with suitable fixtures such as clamps or platforms with indentations to hold a loose gemstone or gemstones, as well as a piece of jewelry containing one or more gemstones such as diamonds. The light from light source 310 in one embodiment is highly focused on the crystal surface of the gemstone.

In one embodiment, CVD diamonds will fluoresce, producing a PL light. This produced light is returned back to the optical fiber 315, which branches into a second type of fiber 325 optimized to transmit wavelengths corresponding to the PL light.

The presence of N-V centers would result in emission bands centered at about 575 and/or 637 nm, and the second type of fiber 325 may be used to carry such emissions to a spectrometer 330 to perform detection of these wavelengths. The fibers 315 and 325 diverge at a junction 335 such that each may carry it corresponding light independently of the other.

In one embodiment, a thermoelectric cooler may be used to cool the gemstone. The cooler may be integrated with the holder 320 in one embodiment. The spectrometer 330 may contain suitable electronics and metering to indicate the nature and type of the diamond from the detected PL light. In some embodiments, the spectrometer 330 may be used in conjunction with microscopic examination to confirm the natural or CVD origins of the gemstone. Further filtering of wavelengths may also be used to detect treated natural stones or high pressure high temperature created stones. In a further embodiment, handling of the stones may be automated so that they could be continuously measured and recorded without human handling.

In further embodiments, a light splitter may be used at 335 to separate wavelengths in fibers 315 and 325 to ensure that the light from light source 310 and the PL light from the diamond fluorescence are separated. In one embodiment, the components are mounted on a substrate, such as a board or other supportive material, and a suitable covering may be used to eliminate stray room light from entering the system, and keep laser light from straying to the outside. Safety interlocks may be provided to shut down the light source in the event the cover is removed. Holder 320 may be made large enough to hold several sizes of stones. Control circuitry and sensors may be included to indicate a pass, fail, or further inspection notice for the tester.

Figure 4:
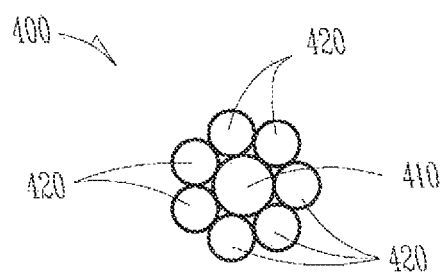
FIG. 4 is a cross section representation of combined fibers according to an example embodiment.

FIG. 4 is a cross section representation of combined fibers 315 and 325 from FIG. 3 represented generally at 400. In one embodiment, fiber 315 is represented as a single fiber at 410, surrounded by multiple fibers 325, as represented with reference number 420. This cross section illustrates the combined fibers taken along lines 4-4 in FIG. 3. The fibers are then separated at junction 335 to provide independent paths for the generated and emitted light.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

What is claimed is:

1. A method comprising:
   placing a diamond on a top surface of a holder;
   cooling the top surface of the holder to cool the diamond below room temperature;
   exposing the cooled diamond to short wavelength light to cause a chemical vapor deposition formed diamond to fluoresce; and
   identifying the diamond as a chemical vapor deposition formed diamond as a function of the fluorescence.

2. The method of claim 1 wherein the diamond is cooled by a thermoelectric cooler.

3. The method of claim 1 and further comprising filtering the fluorescence from the diamond with a filter prior to identifying the diamond.

4. The method of claim 3 wherein the filter provides emitted light from the gemstone to the detector when the gemstone is a CVD grown gemstone.

5. The method of claim 1 wherein the light is provided by a short wavelength laser.

6. The method of claim 5 wherein fluorescence at wavelength(s) near 575 and near 637 nm are indicative of chemical vapor deposition formed diamond.

7. A system comprising:
   a radiation source to provide short wavelength light;
   a holder having a top surface on which to position a table of a gemstone to receive the light;
   detector positioned to receive fluorescent light from the gemstone when the gemstone is a CVD grown gemstone; and
   a cooling device positioned to cool the top surface of the holder to cool a gemstone positioned on the top surface of the holder.

8. The system of claim 7 and further comprising a lens coupled between the radiation source and the holder.

9. The system of claim 7 wherein the cooling device is a thermoelectric cooler.

10. The system of claim 7 and further comprising a filter positioned between the holder surface and the detector.

11. The system of claim 10 wherein the filter provides emitted light from a gemstone positioned on the holder surface to the detector when the gemstone is a CVD grown gemstone.

12. The system of claim 7 wherein the radiation source comprises a short wavelength laser.

13. The system of claim 12 wherein the detector is adapted to detect light with wavelength(s) near 575 and/or 637 nm.

14. A system comprising:
   a radiation source to provide short wavelength light;
   a first optical fiber optically coupled to the radiation source;
   a holder having an integrated cooling device to position a table of a gemstone to receive the light from the first optical fiber;
   the cooling device coupled to cool a gemstone positioned in the holder;
   a second optical fiber optically coupled to receive fluorescent light from the gemstone when the gemstone is a CVD grown gemstone; and a detector positioned to receive the fluorescent light from the second optical fiber to detect the fluorescent light to identify a gemstone as a CVD grown gemstone.

15. The system of claim 14 wherein the integrated cooling device includes a thermoelectric cooler.

16. The system of claim 14 wherein the radiation source comprises a short wavelength laser.

17. The system of claim 16 wherein the detector is adapted to detect light with wavelength(s) near 575 and/or 637 nm.

18. The system of claim 17 wherein the second optical fiber comprises multiple optical fibers wrapped around the first optical fiber for at least a portion of the length of the first optical fiber.

19. The system of claim 17 wherein the first and second optical fibers are adapted to carry light from the light radiation source and emitted from the gemstone respectively.

20. The system of claim 14 wherein the holder includes a top surface including indentations to hold diamonds.

* * * * *

UNITED STATES PATENT AND TRADEMARK OFFICE
CERTIFICATE OF CORRECTION

| | | |
|---|---|---|
| PATENT NO. | : 8,553,208 B2 | Page 1 of 1 |
| APPLICATION NO. | : 13/491301 | |
| DATED | : October 8, 2013 | |
| INVENTOR(S) | : Linares et al. | |

It is certified that error appears in the above-identified patent and that said Letters Patent is hereby corrected as shown below:

In the Specification

In column 1, line 27, delete "cvd" and insert --CVD--, therefor

In column 1, line 34, delete "cvd" and insert --CVD--, therefor

In column 1, line 51, delete "cvd" and insert --CVD--, therefor

In column 2, line 27, delete "fitter" and insert --filter--, therefor

In column 2, line 33, delete "light, in" and insert --light. In--, therefor

In column 2, line 61, delete "cvd" and insert --CVD--, therefor

In column 3, line 17, after "light", insert --.--, therefor

In the Claims

In column 4, line 36, in Claim 7, before "detector", insert --a--, therefor

In column 5, line 15, in Claim 19, after "the", delete "light", therefor

Signed and Sealed this
Eleventh Day of November, 2014

Michelle K. Lee
*Deputy Director of the United States Patent and Trademark Office*